United States Patent [19]

Kolts et al.

[11] Patent Number: 4,672,145
[45] Date of Patent: Jun. 9, 1987

[54] COMPOSITION OF MATTER AND METHOD OF OXIDATIVE CONVERSION OF ORGANIC COMPOUNDS THEREWITH

[75] Inventors: John H. Kolts, Ochelata; Jack P. Guillory, Bartlesville, both of Okla.

[73] Assignee: Phillips Petroleum Company, Bartlesville, Okla.

[21] Appl. No.: 713,674

[22] Filed: Mar. 19, 1985

[51] Int. Cl.$^4$ .............................................. C07C 5/48
[52] U.S. Cl. ................................. 585/658; 502/340; 502/344; 502/352; 585/443; 585/444; 585/500; 585/661; 585/943
[58] Field of Search ............... 502/340, 344, 341, 352; 585/654, 657, 658, 943, 500, 443, 440, 441, 444, 445, 660, 661

[56] References Cited

U.S. PATENT DOCUMENTS

| | | | |
|---|---|---|---|
| 3,446,865 | 5/1969 | Roth et al. | 585/440 |
| 3,586,733 | 6/1971 | Connor et al. | 585/658 |
| 3,767,567 | 10/1973 | Tomita et al. | 585/653 |
| 3,789,078 | 1/1974 | Nolan et al. | 585/443 |
| 3,793,391 | 2/1974 | Bertus | 585/658 |
| 3,925,499 | 12/1975 | Pitzer | 585/443 |
| 4,093,536 | 6/1978 | Heckelsberg | 585/653 |
| 4,159,970 | 7/1979 | Heckelsberg | 502/324 |
| 4,176,140 | 11/1979 | Bertus et al. | 585/661 |
| 4,308,167 | 12/1981 | Sugiyama et al. | 502/340 |
| 4,375,571 | 3/1983 | Hart et al. | 585/440 |
| 4,409,417 | 10/1983 | Herbstman | 585/654 |
| 4,444,984 | 4/1984 | Jones et al. | 585/654 |
| 4,450,310 | 5/1984 | Fox et al. | 585/400 |
| 4,450,313 | 5/1984 | Eastman et al. | 585/624 |
| 4,495,374 | 1/1985 | Jones et al. | 585/500 |
| 4,497,971 | 2/1985 | Eastman et al. | 585/658 |
| 4,499,322 | 2/1985 | Jones et al. | 585/654 |
| 4,523,045 | 6/1985 | Jones et al. | 585/500 |
| 4,523,049 | 6/1985 | Jones et al. | 585/500 |
| 4,544,786 | 10/1985 | Breder et al. | 585/658 |
| 4,547,611 | 10/1985 | Jones et al. | 585/658 |

FOREIGN PATENT DOCUMENTS 3237079  4/1982  Fed. Rep. of Germany ...... 585/500

OTHER PUBLICATIONS

Keller et al, J. Catalysis, 73, 9–19 (1982).

*Primary Examiner*—Asok Pal
*Attorney, Agent, or Firm*—C. F. Steininger

[57] ABSTRACT

A solid composition of matter consisting essentially of:
(a) a component comprising: (1) at least one metal selected from the group consisting of Group IA metals and compounds containing said metals and (2), optionally, at least one material selected from the group consisting of tin, compounds containing tin, chloride ions and compounds containing said chloride ions and
(b) a component comprising at least one metal selected from the group consisting of Group IIA metals and compounds containing said metals.

The composition is particularly useful as a contact material for the oxidative conversion of less valuable organic compounds to more valuable organic compounds, particularly in the presence of a free oxygen containing gas. A method for converting feed organic compounds to product organic compounds, in the presence of a free oxygen containing gas, utilizing the above composition, as well as combinations of tin and a Group IIA metal and of tin, chloride ions and a Group IIA metal is disclosed, particularly the oxidative dehydrogenation of $C_2$ to $C_7$ alkanes to olefins.

20 Claims, No Drawings

COMPOSITION OF MATTER AND METHOD OF OXIDATIVE CONVERSION OF ORGANIC COMPOUNDS THEREWITH

The present invention relates to an improved composition of matter. In a more specific aspect, the present invention relates to an improved solid contact material for the oxidative conversion of feed organic compounds to product organic compounds. In yet another aspect, the present invention relates to a solid contact material for the oxidative conversion of feed organic compounds to product organic compounds, in the presence of a free oxygen containing gas and a method for such conversion.

BACKGROUND OF THE INVENTION

Numerous processes are in use and have been proposed for the conversion of organic compounds and feedstocks to more valuable organic compounds and more valuable feedstocks for use in the organic chemical and petrochemical industries, particularly organic compounds and feedstocks derived from petroleum sources.

One promising approach to such conversion has been the oxidative conversion of organic compounds to other organic compounds. However, in many cases, such oxidative conversion processes are not commercially viable, primarily because they are energy intensive, conversions of the feedstock are low, selectively to the desired compounds is low and such processes cannot be utilized in a continuous manner. In most of such processes the feedstocks are contacted with a solid contact material. However, there is a difference of opinion among workers in the art concerning the nature of such processes, and, particularly, the function of the contact material and the manner in which such function is performed. For example, workers in the art have at one time or another suggested that the function of the contact material involves a purely physical phenomenon, an adsorption-desorption process, either of atomic or molecular oxygen, either on the surface or occluded within the solid material, oxidation-reduction, utilizing multivalent metals capable of oxidation-reduction, adsorption and desorption of the organic materials on the solid materials, a free radical mechanism, etc. Consequently, the solid materials utilized are referred to variously as "contact materials", "promoters", "activators" and "catalysts". Accordingly, in order to avoid functional categorization, the terms "solid contact material" or "solid contact materials" will be utilized in the present application.

Since many processes of the prior art are based on the theory that the contact materials function via adsorption-desorption of oxygen, oxidation-reduction, etc., such processes are operated in a cyclic manner by passing an oxidizing gas over the contact material, then contacting the feedstock with the oxygen-containing contact material, and, thereafter, reactivating or regenerating the contact material by again passing an oxidizing gas thereover. Such processes thus require undesirably high temperatures, are energy intensive, since the exothermic and endothermic reactions occur separately, equipment costs are high, because of the necessity for rapid cycling, and the contact material's useful life is comparatively short.

From the above, it is quite clear that the suitability of contact materials for the oxidative conversion of organic compounds is unpredictable. It is, therefore, highly desirable that new and improved contact materials for such use be developed, and that improved processes utilizing such contact materials be provided, particularly processes which lower the temperatures necessary, lower the energy requirements, are capable of being carried out in a continuous manner, extend the useful life of the contact material, improve the conversion of the feedstock and improve the selectively to the desired products.

Of the various feedstocks for the organic chemical and petrochemical industries, olefins, such as ethylene and propylene are of particular interest and have become major feedstocks. Of these, ethylene is by far the more important chemical feedstock since the demand for ethylene feedstocks is about double that for propylene feedstocks.

Consequently, there is a definite need for materials and processes for the conversion of relatively inexpensive feedstocks to ethylene. At the present time, ethylene is produced almost exclusively by the dehydrogenation or pyrolysis of ethane and propane, naphtha and, in some instances, gas oils. about 75% of the ethylene is produced at the present time by steam cracking of ethane and propane derived from natural gas, since natural gas contains from about 5 volume percent to about 60 volume percent of hydrocarbons other than methane, with the majority being ethane. However, relatively severe conditions, particularly temperatures in excess of about 1000° C., are required and, as indicated, such processes are highly energy intensive. In order to reduce the severity of the conditions, particularly temperature, numerous proposals to catalyze pyrolytic reactions have been made. While some of these processes do, in fact, reduce the severity of the conditions, the conversion of the feedstock and the selectively to ethylene are still quite low. Of particular interest in this phase of the art, is the oxidative dehydrogenation of alkanes, particularly alkanes having from 2 to 7 carbon atoms, and, still more particular, ethane. However, many of the processes for oxidative dehydrogenation, which have been proposed, are subject to some or all of the previously mentioned deficiencies.

SUMMARY OF THE INVENTION

It is therefore an object of the present invention to provide an improved composition of matter and method of utilizing the same which overcomes the above and other disadvantages of the prior art. Another object of the present is to provide an improved composition of matter. Yet another object of the present invention is to provide an improved contact material for the oxidative conversion of organic compounds to other organic compounds. Still another object of the present invention is to provide an improved contact material for the oxidative conversion of organic compounds to other organic compounds, in the presence of a free oxygen containing gas. Another and further object of the present invention is to provide an improved method for the oxidative conversion of organic compounds to other organic compounds in the presence of a free oxygen containing gas. Another and further object of the present invention is to provide an improved method for the oxidative conversion of alkane hydrocarbons to other hydrocarbons in the presence of a free oxygen containing gas. A further object of the present invention is to provide a method for the oxidative conversion of organic compounds to other organic compounds having an improved conversion of feedstock. Yet another object of the present invention is to provide a method for the oxidative conversion of organic compounds to other organic compounds having an improved selectively to desired products. A further object of the present invention is to provide a method for the oxidative conversion of organic compounds to other organic compounds having an improved conversion of feedstock and an improved selectivity to desired products. Another and further object of the present invention is to provide a method for the oxidative conversion of organic compounds to other organic compounds which utilizes temperatures below those of known processes. A still further object of the present invention is to provide a method for the oxidative conversion of organic compounds to other organic compounds which reduces the energy requirements thereof. Another object of the present invention is to provide a method for the oxidative conversion of organic compounds to other organic compounds which can be carried out in a continuous manner. Yet another object of the present invention is to provide a method for the oxidative convesion of organic compounds to other organic compounds which extends the useful life of the contact material utilized. These and other objects of the present invention will be apparent from the following detailed description.

The present invention provides an improved, solid composition of matter consisting essentially of:

(a) a component comprising (1) at least one metal selected from the group consisting of Group IA metals, and compounds containing said metals and (2), optionally, at least one material selected from the group consisting of tin, compounds containing tin, chloride ions and compounds containing said chloride ions and (b) a component comprising at least one metal selected from the group consisting of Group IIA metals and compounds containing said metals.

In still another aspect, the present invention relates to a solid contact material, of the specified character, for the oxidative conversion of feed organic compounds to product organic compounds, in the presence of a free oxygen containing gas. The present invention further provides an improved method for the oxidative conversion of feed organic compounds to product organic compounds in which the free organic compounds and a free oxygen containing gas are contacted with a solid contact material, under conditions sufficient to produce such other product organic compounds, and, still more particularly, an improved method for such oxidative conversion of alkane hydrocarbons to other hydrocarbons, desirably ethylene.

DESCRIPTION OF THE PREFERRED EMBODIMENTS

The improved, solid composition of matter of the present invention is a solid composition of matter consisting essentially of:

(a) a component comprising: (1) at least one metal selected from the group consisting of Group IA metals and compounds containing said metals and (2), optionally, at least one material selected from the group consisting of tin, compounds containing tin, chloride ions and compounds containing said chloride ions and (b) a component comprising at least one metal selected from the group consisting of a Group IIA metal and compounds containing said metal.

Particularly useful Group IA metals are selected from the group consisting of lithium, sodium and potassium, and, still more particularly, lithium. Group IIA metals, preferably, are selected from the group consisting of magnesium, calcium, strontium and barium and, still more particularly, magnesium and calcium.

These compositions of matter and contact materials are particularly useful for the oxidative conversion of organic compounds to other organic compounds, and, particularly, the conversion of organic compounds to other organic compounds, in the presence of a free oxygen containing gas. Processes of this character include the oxidative dehydrogenation of hydrocarbons, particularly alkanes having 2 to 7 carbon atoms, to other hydrocarbons, particularly ethylene, the oxidative conversion of methane to higher hydrocarbons, particularly ethylene, the oxidative methylation to toluene, in the presence of methane, to ethyl benzene and styrene, the oxidative conversion of toluene to stilbene, the oxidative methylation of acetonitrile, in the presence of methane, to acrylonitrile and $C_2+$ hydrocarbons and the oxidative methylation of other hydrocarbons. The compositions of matter of the present invention are particularly useful for the oxidative dehydrogenation of alkane hydrocarbons to other hydrocarbons, particularly the oxidative dehydrogenation of alkanes having from 2 to 7 carbon atoms to ethylene, in the presence of a free oxygen containing gas.

The above compositions of matter as well as compositions containing tin in combination with Group IIA metals have been found quite effective for the oxidative conversion of feed organic compounds to product organic compounds, in the presence of a free oxygen containing gas, particularly the oxidative conversion of alkanes having 2 to 7 carbon atoms, as an ethane-containing gas, to olefins, particularly ethylene. Specifically, in accordance with the present invention, feed organic compounds are converted to product organic compounds by contacting feed organic compounds, such as alkanes having 2 to 7 carbon atoms, particularly an ethane-containing gas, and a free oxygen containing gas with a solid composition of matter consisting essentially of:

(a) a component comprising:

(1) at least one metal selected from the group consisting of Group IA metals, tin and compounds containing said metals and (2) optionally at least one material selected from the group consisting of chloride ions and compounds containing said chloride ions and (b) a component comprising:

at least one metal selected from the group consisting of Group IIA metals and compounds containing said metals under conditions sufficient to convert said feed organic compounds to said product organic compounds.

When the term "effective amount" is utilized with reference to the composition of matter and contact material herein, this term is meant to include more than an insignificant amount and, thus, a small amount sufficient to affect the function of the composition of matter for the purpose for which it is to be utilized.

Thus, the above compositions of matter contain from an effective amount of the Group IA metal to near 100 wt. % so long as an effective amount of the Group IIA metal is present, preferably, a minor amount and usually from 0.1 to 50 wt. % of the Group IA metal (expressed as a metal) and, still more preferably, between about 0.5 and about 15 wt. % and, optimally, between about 1 and about 5 wt. %. Where tin is utilized, it is present in an effective amount to near 100 wt. %, usually in amounts between about 0.5 and 20 wt. %, and, preferably, between about 1 and about 7 wt. %. Chloride, when present, is utilized in amounts from an effective amount to near 100 wt. %, usually between about 0.1 and about 5 wt. %, expressed as elemental chlorine. The weight percent designations given are the weight percent of the indicated element based on the total weight of the solid composition of matter or contact material, including the Group IIA metal compound and the compound or compounds in which the element or elements are present.

The above-mentioned components can be mixed with or deposited on an "inert support material" adapted to harden or support the active materials. The term "inert support material", when utilized in this context, is meant to include any material which does not react with or exchange ions with the active components, has no significant functional effect on the production of desired or undesired products in the process for which the solid contact material is utilized and functions only as a hardening agent or support for the active components. Where such solid support material is utilized the weight of such solid support material is not included in determining the relative weights of the active components.

The Group IA metal, tin, and Group IIA metal can be derived from any suitable source of such materials, such as metal carbonates, oxides, nitrates, octoates and chlorides. The chlorine may be an organic or inorganic chloride. The compositions of matter can be prepared by any suitable method known in the art for the preparation of such materials in solid form. Particularly effective techniques are those utilized for the preparation of solid catalysts. Conventional methods include coprecipitation from an aqueous, an organic or a combination solution-dispersion, impregnation, dry mixing, wet mixing or the like, alone or in various combinations. In general, any method can be used which provides compositions of matter containing the prescribed components in effective amounts. For example, a lithium/magnesium material may be produced by mixing lithium carbonate and magnesium oxide in a blender with enough water to form a thick slurry. The slurry can then be dried, usually at a temperature sufficient to volatilize the water or other carrier, such as about 220° F. to about 450° F. Alternatively, magnesium oxide pellets can be impregnated with an aqueous solution of lithium nitrate and dried. Where tin is present, the composition can be produced by impregnating magnesium oxide pellets with a hexane solution of tin octoate and drying. Lithium/tin/magnesium compositions can be produced by impregnating magnesium oxide pellets with a hexane solution of tin octoate and an aqueous solution of lithium nitrate and drying. In all cases, irrespective of how the components are combined, and irrespective of the source of the metal or chloride, the dried composition is calcined in the presence of a free oxygen containing gas, usually at temperatures between about 700° F. and about 1200° F. for from 1 to about 24 hours. While the exact form of the metals in the resultant composition is not known, it is believed that the Group IA and Group IIA metals are predominantly in their oxide form and, where chlorine is present, it is in the form of a chloride. Where both tin and chloride ions are present they can be added in the form of tin chloride.

The oxidative dehydrogenation of alkanes to other hydrocarbons, particularly ethane to ethylene, can be carried out under a wide range of conditions. Since conditions which favor high conversion of feedstock generally result in lower selectivities to the desired products, and vice versa, the conversion and selectivity can be balanced, as desired, to some extent, by selecting the composition of the contact material, and/or varying the conditions of operation.

In any event, the feed rate of the hydrocarbon feedstock will generally be between about 100 and about 1000 GHSV, and, preferably, between about 400 and about 500 GHSV. When air is, utilized as a source of free oxygen, a feed rate of about 200 to about 10,000 GHSV and preferably about 1200 to 1500 GHSV is utilized. The volumetric ratio of gaseous feed components, specifically ethane to free oxygen, will be between about 1/1 and about 30/1 and preferably 1/1 and about 3/1. Inert gases such as nitrogen, helium and the like can be utilized as a diluent or a substitute for the nitrogen of air, when the free oxygen containing gas is oxygen or an oxygen-enriched air. Reaction temperatures may vary between about 600° C. and about 775° C., and are, preferably, between about 650° C. and 725° C. Total pressures may vary from about 0.5 to about 10 atmospheres and are preferably around 1 atmosphere.

The nature and the advantages of the present invention are illustrated by the following examples of the oxidative dehydrogenation of ethane, in the presence of a free oxygen containing gas.

A contact material comprising magnesium oxide alone was prepared by calcining magnesium oxide pellets at 815° C. in the presence of air. Lithium/magnesium oxide contact materials were prepared by impregnating 50 grams of magnesium oxide pellets with 2.1 grams lithium nitrate dissolved in 50 milliliters of water. After impregnation, the contact material was dried at 120° C. and then calcined for 3 hours at 815° C. in air. This resulted in the contact material having a calculated lithium content of 0.5 wt. %. A tin/magnesium oxide contact material was prepared by impregnating 40 grams of magnesium oxide with 4.35 grams of tin octoate dissolved in 60 milliliters of hexane. The composition was then dried and calcined at 815° C. for 3 hours in air. This resulted in a material having 2.5 wt. % of tin. A lithium/tin/magnesium oxide contact material was prepared by impregnating 40 grams of magnesium oxide with 4.35 grams of tin octoate dissolved in 60 milliliters of hexane, drying the same and, thereafter, impregnating with 2.1 grams of lithium nitrate dissolved in 60 milliliters of water. The contact material was again dried and calcined for 3 hours at 815° C. in air. This contact material contained 6.3 wt. % lithium and 2.5 wt. % tin. A contact material of tin/chloride/magnesium oxide was prepared by impregnating 40 grams of magnesium oxide with 10.7 grams of tin chloride (Sn Cl$_4$) dissolved in 50 ml of water. The resultant material was dried at 100° C. and then calcined at 815° C. This contact material was calculated to contain 8.2 wt. % tin and 0.5 wt. % chlorine. Finally, a contact material of lithium/tin/chloride/magnesium oxide was prepared by impregnating 40 grams of magnesium oxide with 10.5 grams tin chloride (Sn Cl$_4$.H$_2$O) dissolved in 50 milliliters of water, drying the same, then impregnating with 2.1 grams of lithium nitrate dissolved in 50 milliters of water, again drying and calcining for 3 hours at 815° C. in air. The calculated content of this contact material was 8.2 wt. % tin and 0.5 wt. % lithium. Atomic absorption analysis showed the catalyst to contain 20 wt. % tin, 1.1 wt. % lithium and 4.7 wt. % chlorine.

These contact materials were then utilized to produce ethylene from ethane by oxidative dehydrogenation. Fifteen milliliter portions of the contact materials (screened to −16 to +40 mesh) were placed in a quartz reactor having a temperature controlled furnace. Gases were flowed through the contact material in a down-flow fashion. Nitrogen was first flowed through the contact material to heat the same to about 700° C. The nitrogen was stopped and a mixture of air and ethane was then flowed over the contact material at 400 GHSV ethane and 1200 GHSV air. Snap samples were taken at appropriate times and analyzed by chromatographic analysis. The results of these runs are shown in the following table.

TABLE I

| Contact Material* | GHSV Total | Vol $C_2H_6/O_2$ | Temp. °C. | Time min. | % Conversion $C_2$ | % Selectivity $C_2^=$ | % Yield $C_2^=$ |
|---|---|---|---|---|---|---|---|
| MgO (Control) | 1600 | 1.67/1 | 700 | 60 | 30.6 | 55.9 | 17.11 |
| MgO (Control) | 1600 | 1.67/1 | 700 | 660 | 25.7 | 54.1 | 13.90 |
| 0.5 Li/MgO | 1600 | 1.67/1 | 700 | 60 | 55.6 | 92.1 | 51.21 |
| 0.5 Li/MgO | 1600 | 1.67/1 | 700 | 960 | 32.5 | 92.6 | 30.10 |
| 2.5 Sn/MgO | 1600 | 1.67/1 | 700 | 60 | 60.9 | 68.3 | 41.59 |
| 2.5 Sn/MgO | 1600 | 1.67/1 | 700 | 120 | 60.0 | 68.0 | 40.80 |
| 6.3 Li/2.5 Sn/MgO | 1600 | 1.67/1 | 700 | 60 | 47.3 | 85.6 | 40.49 |
| 8.2 Sn/0.5 Cl/MgO | 1600 | 1.67/1 | 700 | 60 | 80.6 | 72.3 | 58.27 |
| 1.1 Li/20 Sn/ 4.7 Cl/MgO | 1600 | 1.67/1 | 700 | 60 | 61.6 | 94.6 | 58.27 |
| 1.1 Li/20 Sn/ 4.7 Cl/MgO | 1600 | 1.67/1 | 700 | 240 | 35.7 | 96.3 | 34.38 |

*All contact materials are in weight percent of the indicated element based on the total weight of MgO and the compound or compounds in which the element or elements are contained.

It is quite apparent from the foregoing table that the contact materials containing lithium, tin, lithium/tin, tin/chloride and lithium/tin/chloride were all vastly superior to magnesium oxide alone, both in the conversion of ethane and the selectivity to ethylene. Comparison of the contact materials containing chloride with those not containing chloride shows that chloride further enhanced the activity of the contact materials. Chloride analysis of the contact material containing lithium/tin/chloride, following four hours of use, showed the chloride concentration had decreased to about 0.3 wt. %. A very distinct advantage of the contact material of the present invention and the process is that the process can be carried out in a continuous manner and, as such, can normally be operated at lower temperatures than conventional, alternate ethane and air, has reduced energy requirements, since the exothermic and endothermic steps occur simultaneously, as opposed to separately as in a cyclic operation where the hydrocarbons and oxygen-containing gas are sequentially passed through the contact material, has reduced commercial construction costs, since there is no need for rapid recycle and cycling, can use a fixed bed reactor and can extend the useful life of the contact material.

The present invention is further illustrated by the following examples, utilizing contact materials of the present invention, for the oxidative conversion of methane to ethane and ethylene, particularly the latter, in the presence of a free oxygen containing gas.

The solid contact materials utilized in the examples were prepared by mixing the ingredients, for example, lithium carbonate and calcium hydroxide, in a blender with enough water to form a thick slurry. The material was calcined overnight at 300° C. and, thereafter, for four hours at 775° F. to produce a contact material containing the specified weight percent of the component present in a minor amount, for example 3 wt. % lithium.

In the runs of the examples, the contact material was loaded in a quartz reactor having a thermocouple well centered in the contact material bed. The reactor was brought up to temperature under nitrogen or air and, thereafter, methane and air (or oxygen) flow was begun. The gas inlet system included electronic flow measurement, a three-zone furnace for heating reactant gases and the contact material and a downstream analysis system. The reactor effluent was snap sampled at any desired time and analyzed for all paraffins and olefins between $C_1$ and $C_4$ and $N_2$, $O_2$, CO and $CO_2$ by gas chromatography. All contact materials are referred to in terms of weight percent of the designated element based on the total weight of the contact material.

The variables and results of this series of tests are set forth in the Table below. Conversion is percent of methane converted. Selectivity and yields are based on mole percent of methane feed converted to a particular product. The $CH_4$ rate can be expressed as cc/min/cc of contact material. For example, when 70 cc/min of $CH_4$ was fed to a reactor containing 20 cc of catalyst the flow rate would be 3.5 cc/min of $CH_4$/cc of contact material. The volumetric ratio of $CH_4$ to oxygen is also parenthetically given in terms of cc/min of $CH_4$ per cc/min of other gases (air or $N_2$) percent. The active metals of the contact materials, which are present in minor amounts, were in their oxide form and, as previously indicated, the percent of such active metal listed is the weight percent of elemental active metal based on the total weight of the active metal compound and the base metal compound.

TABLE II

| Run No. | Contact Material | Vol., cc $CH_4$/Air | Vol. of Con. Mat | Sample Time (min) | Temp. (°C.) | Conversion | Selectivity | | | | | | | Conversion To | | |
|---|---|---|---|---|---|---|---|---|---|---|---|---|---|---|---|---|
| | | | | | | | $C_2^=$ | $C_2$ | $C_2$'s | $C_3^=$ | $C_3$ | $CO_2$ | CO | $C_2^=$ | $C_2$'s | HC's |
| 1 | MgO | 70/80 | 20 cc | 6 | 700 | 14.5 | 8.5 | 10.1 | 18.6 | — | — | 51.3 | 30.1 | 1.23 | 2.70 | 2.70 |
| | | | | 60 | 705 | 15.7 | 6.8 | 8.9 | 15.7 | 0.1 | — | 54.7 | 29.5 | 1.07 | 2.46 | 2.48 |

TABLE II-continued

| Run No. | Contact Material | Vol., cc CH4/Air | Vol. of Con. Mat | Sample Time (min) | Temp. (°C.) | Conversion | Selectivity C2= | C2 | C2's | C3= | C3 | CO2 | CO | Conversion To C2= | C2's | HC's |
|---|---|---|---|---|---|---|---|---|---|---|---|---|---|---|---|---|
| 2 | Na(3%)/MgO | 70/80 | 20 cc | 5 | 710 | 20.2 | 29.5 | 22.9 | 52.4 | 2.7 | 0.9 | 41.3 | 2.6 | 5.96 | 10.52 | 11.31 |
|   |   |   |   | 45 | 716 | 20.2 | 31.2 | 22.5 | 53.7 | 2.9 | 0.9 | 39.5 | 3.0 | 6.30 | 10.85 | 11.62 |
|   |   |   |   | 80 | 716 | 19.1 | 33.2 | 23.8 | 57.0 | — | — | 39.7 | 3.2 | 6.34 | 10.89 | 10.89 |
| 3 | Li(3%)/CaO | 70/80 | 20 cc | 17 | 707 | 18.0 | 40.9 | 27.3 | 68.0 | 3.7 | — | 25.3 | 2.7 | 7.36 | 12.24 | 12.91 |
|   |   |   |   | 53 | 711 | 19.0 | 38.7 | 28.6 | 67.3 | 3.7 | 1.0 | 24.9 | 3.1 | 7.35 | 12.79 | 13.68 |
|   |   |   |   | 90 | 711 | 18.0 | 38.3 | 26.6 | 64.9 | 3.8 | 1.1 | 26.9 | 3.4 | 6.89 | 11.68 | 12.56 |
|   |   |   |   | 1050 | 710 | 17.3 | 36.0 | 25.8 | 61.8 | 3.2 | — | 29.9 | 5.1 | 6.23 | 10.69 | 11.25 |
| 4 | Na(3%)/CaO | 70/80 | 20 cc | 70 | 731 | 18.9 | 36.1 | 29.2 | 65.3 | 3.4 | 2.0 | 27.3 | 1.9 | 6.82 | 12.34 | 13.36 |
|   |   |   |   | 120 | 709 | 15.7 | 35.3 | 35.0 | 70.3 | 2.9 | 2.2 | 24.6 | — | 5.54 | 11.04 | 11.84 |
|   |   | 50/100 | 20 cc | 5 | 717 | 21.7 | 36.0 | 25.8 | 61.8 | 2.8 | 1.6 | 31.8 | 1.9 | 7.81 | 13.41 | 14.37 |
|   |   |   |   | 40 | 719 | 21.8 | 38.4 | 28.2 | 66.6 | 2.8 | — | 28.4 | 2.2 | 8.37 | 14.52 | 15.13 |
| 5 | K(3%)/CaO | 100/100 | 25 cc | 6 | 710 | 10.7 | 19.5 | 36.0 | 55.5 | 1.1 | 1.7 | 36.0 | 2.6 | 2.09 | 5.94 | 6.24 |
|   |   |   |   | 51 | 704 | 8.5 | 19.9 | 44.8 | 64.7 | — | — | 35.3 | — | 1.69 | 5.50 | 5.50 |
|   |   |   |   | 96 | 702 | 9.8 | 19.0 | 38.9 | 57.9 | 1.2 | 1.9 | 36.1 | 2.8 | 1.86 | 5.67 | 5.98 |
|   |   |   |   | 130 | 700 | 9.9 | 19.5 | 38.6 | 58.1 | — | — | 39.0 | 2.9 | 1.93 | 5.75 | 5.75 |
| 6 | Li(3%)/CaO | 70/80 (CH4/N2) | 20 cc | 40 | 703 | 0.28 | — | — | — | — | — | 100 | — | — | — | — |
|   |   |   |   |   | 703 | 0.28 | — | — | — | — | — | 100 | — | — | — | — |
|   |   |   |   |   | 702 | 0.06 | — | — | — | — | — | 99.99 | — | — | — | — |
| 7 | Quartz | 70/80 | 20 cc | 40 | 740 | 0.00 | — | — | — | — | — | — | — | — | — | — |

While specific materials, equipment, conditions and modes of operation have been set forth herein, it is to be understood that these specific recitals are by way of illustration and to set forth the best mode only, and are not to be considered limiting.

That which is claimed:

1. A method for the dehydrogenation of saturated feed hydrocarbons having from 2 to 7 carbon atoms per molecule to product organic compounds, comprising:
    contacting said feed hydrocarbons and a free oxygen containing gas with a solid contact material, consisting essentially of:
    (a) at least one metal selected from the group consisting of Group IA metals and tin and compounds containing the same and
    (b) at least one metal selected from the group consisting of Group IIA metals and compounds containing the same,
    under conditions sufficient to convert said feed hydrocarbons to said product organic compounds.

2. A method in accordance with claim 1 wherein the Group IA metal is selected from the group consisting of lithium, sodium and potassium.

3. A method in accordance with claim 1 wherein the Group IA metal is lithium.

4. A method in accordance with claim 1 wherein the Group IIA metal is selected from the group consisting of magnesium, calcium, strontium and barium.

5. A method in accordance with claim 1 wherein the Group IIA metal is magnesium.

6. A method in accordance with claim 1 wherein the Group IIA metal is calcium.

7. A method in accordance with claim 1 wherein the Group IA metal is predominantly in the oxide form.

8. A method in accordance with claim 2 wherein the Group IA metal is predominantly in the oxide form.

9. A method in accordance with claim 1 wherein the tin is predominantly in the oxide form.

10. A method in accordance with claim 1 wherein the Group IA metal and tin are predominantly in the oxide form.

11. A method in accordance with claim 1 wherein both tin and chloride ions are present in the solid contact material in the form of tin chloride.

12. A method in accordance with claim 1 wherein the Group IA metal is present in an amount between about 0.1 and about 50 wt. %, expressed in terms of the element, based on the total weight of the contact material.

13. A method in accordance with claim 1 wherein the tin, when present, is present in an amount between about 0.5 to about 20 wt. %, expressed in terms of the element, based on the total weight of the contact material.

14. A method in accordance with claim 1 wherein the feed organic compounds and the product organic compounds are hydrocarbons.

15. A method in accordance with claim 1 wherein the feed organic compounds are an ethane-containing gas.

16. A method in accordance with claim 1 wherein the oxygen to ethane ratio is between about 1/1 to 30/1.

17. A method in accordance with claim 1 wherein the contacting step is carried out at a temperature between about 600° C. and about 775° C.

18. A method in accordance with claim 1 wherein the product organic compounds contain significant amounts of ethylene.

19. A method in accordance with claim 1 wherein the contact material additionally consists essentially of chloride ions and compounds containing chloride ions.

20. A method in accordance with claim 19 wherein the chloride is present in an amount between about 0.1 to about 5 wt. %, expressed in terms of elemental chlorine, based on the total weight of the contact material.

* * * * *